Dec. 12, 1939. D. AICARDI Plant Pat. 349
ROSE PLANT
Filed April 17, 1939
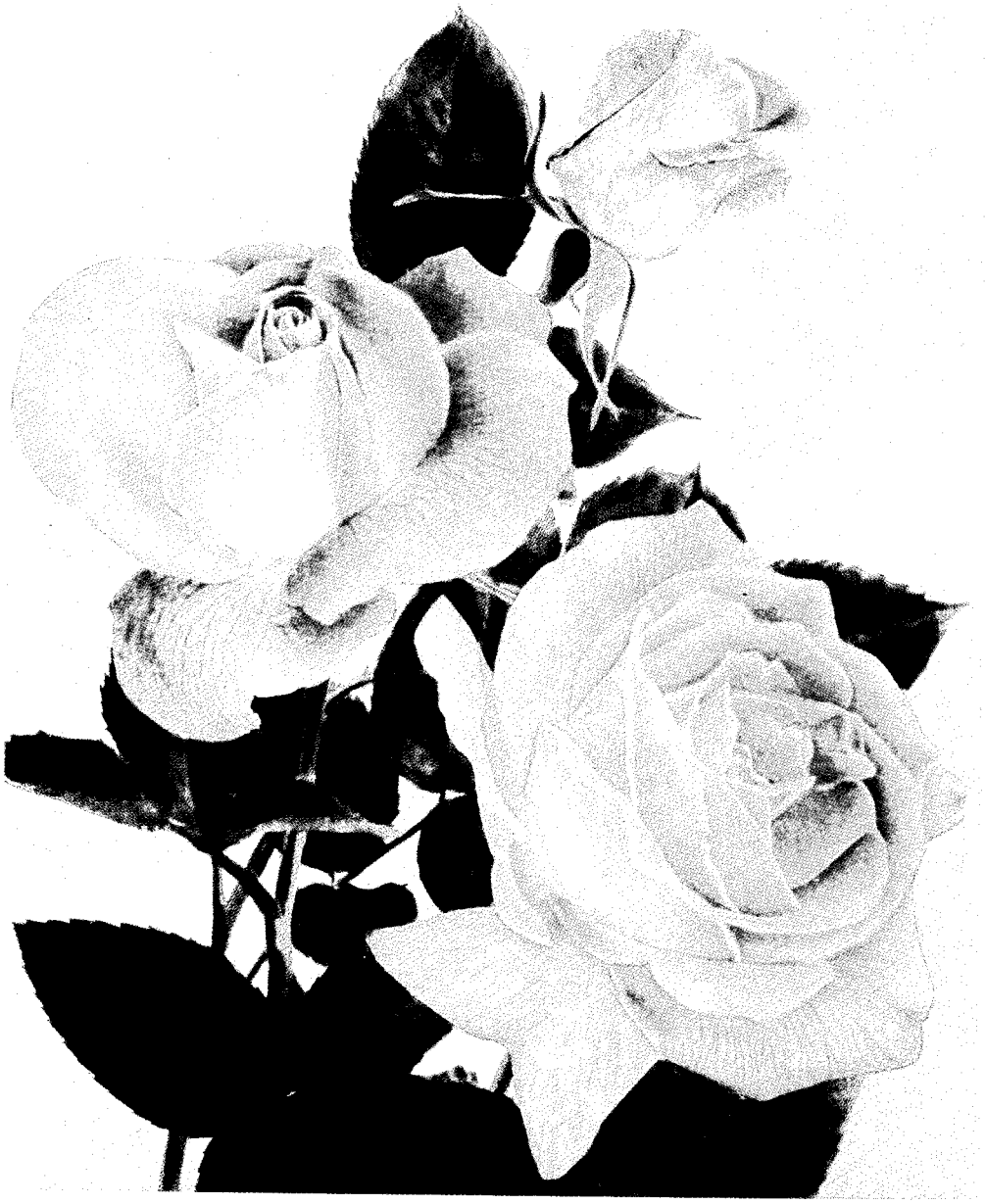
Inventor
D Aicardi
By Robb & Robb
Attorneys Patented Dec. 12, 1939

Plant Pat. 349

UNITED STATES PATENT OFFICE

349

ROSE PLANT

Domenico Aicardi, San Remo, Italy, assignor to Jackson & Perkins Company, Newark, N. Y.

Application April 17, 1939, Serial No. 268,403

1 Claim. (Cl. 47—61)

This invention relates to a new and distinct variety of Hybrid Tea rose, the result of a cross between Julien Potin and Sensation.

As is well known, Julien Potin is considered to be one of the best yellow varieties marked by its pure primrose-yellow, fragrant flowers coming abundantly upon a worth-while plant while Sensation is noted for its large size, scarlet-crimson blossoms.

The objective of the cross in the present instance was the origination of a new rose having certain of the desirable characteristics of its parents. The result of this hybridization is the production of a flower of startling color combination as shown in the accompanying illustration in three stages of development and essentially distinct as regards either its parents or others of similar character.

More specifically, this new variety is characterized by (1) the intensity of the color of its flower with its rich contrast between red of the inside and fold and yellow on the outside of its petals; (2) its penetrating sweet, persistent fragrance; (3) very large size and constancy of bloom, and (4) its lustrous contrasting dark green foliage.

Other minor or less important distinctions will be noted in the following specific description of the variety in which the color terminology employed is given in accordance with Ridgway's Color standard, the primary characteristics referred to being found to be fixed in the asexual reproductions of the plant:

Parentage:

*Seed parent.*—Julien Potin.

*Pollen parent.*—Sensation.

Classification:

Botanic and commercial—Hybrid Tea.

*Flower*

Blooming habit:

Observations made at Newark, New York, in September, 1938.

Blooms once—profusely.

Recurrent—intermittent.

Bud:

*Size.*—Large.

*Form.*—Long, pointed; unaffected by wet or hot weather.

*Color.*—When sepals first divide—Oxblood Red, Plate I. When petals begin to unfurl—Carmine, Plate I. When half blown: inside of petals—between said Carmine and Nopal Red, Plate I; reverse of petals—Light Jasper Red, Plate 13; base of petals Light Cadmium, Plate 4, which is suffused into Light Jasper Red, Plate 13.

*Sepals.*—Serrated branched—extend beyond the bud forming a small hood. Curl back when bud half open.

*Calyx.*—Shape—ovoid funnel shape. Size—long, slender. Aspect—smooth. Odor when rubbed—resembles faintly the odor of lemon skin.

*Peduncle.*—Length—medium. Aspect—smooth. Color—Rainette Green, Plate 31. Strength—stiff, erect, heavy.

*Opening.*—Bud opens well. Is not affected by adverse conditions.

Bloom:

*Size.*—Very large. Average size when fully expanded 6".

*Borne.*—Singly.

*Stems.*—Medium length; normal strength.

*Form.*—When first open—high center; outer petals curl back.

*Petalage.*—Double (full but open center). Number of petals under normal conditions—20.

*Color.*—Center of flower—Mikado Orange, Plate 3, suffusing to Begonia Rose, Plate 1, towards tips of petals. Outer petals—between Nopal Red, Plate I, and Begonia Rose, Plate 1. Base of petals (aiglet)—Light Cadmium, Plate 4. Inside of petals—Spectrum Red, Plate 1. Reverse of petals—Light Jasper Red, Plate 13; base of petal—Light Cadmium, Plate 4, which is suffused into Light Jasper Red, Plate 13. General tonality from a distance—Scarlet Red.

*Variegations.*—None.

*Discoloration.*—General tonality at end of first day—Scarlet Red (Plate I). Second day—inner petals Begonia Rose—outer petals Rose Red (Plate 12). Third day—inner petals Begonia Rose—outer petals Rose Red Color (Plate 12). The gentle fading specified distinctively novel.

Petals:

*Texture.*—Thick. Unaffected by wet or hot weather.

*Appearance.*—Inside—velvety; outside—shiny.

*Form.*—Oval.

*Arrangement.*—Informal (with "rags" in center). Petaloids in center—few, small.

*Persistence.*—Drop off cleanly.

*Fragrance.*—Strong. Nature—fruity (Russet apple). Sweet, strong fragrance lasting throughout all stages of flowers.

*Lasting quality.*—On the plant, long; as cut flower, long.

Genital organs:

*Stamens, anthers.*—Medium size, many. Color—Light Cadmium Yellow edged with Aniline Yellow, Plate 4. Arrangement—Regular round styles.

*Stamens, filaments (threads).*—Long. Color—Scarlet, Plate I.

*Pollen.*—Apricot Yellow, Plate 4.

*Styles.*—Bunched, uneven length, short, thin. Scarlet, Plate 1.

*Stigmas.*—Empire Yellow.

*Ovaries.*—All enclosed in calyx.

Fruit:

Variety is seldom fertile with its own pollen.

*Form.*—Flat headed.

*Aspect.*—Smooth.

*Sepals.*—Recurved.

*Plant*

Form:

Bush.

Growth:

Not very heavy—branching, wood somewhat lighter than that of other similar varieties—uniform and rather rounded; vigorous. Medium tall growth, not heretofore found in the color combination of foliage described.

Foliage:

Three to five leaflets.

*Size.*—Medium.

*Quantity.*—Normal.

*Color.*—New foliage—upper side, edges Vandyke Red, Plate 13; center, Cress Green, Plate 31; under side—Light Cress Green, Plate 31. Old foliage: upper side—Dark Cress Green, Plate 31; under side—Cress Green, Plate 31.

*Shape.*—Oval.

*Texture.*—Upper side—glossy. Under side—smooth. Ribs and veins—prominent.

*Edge.*—Serrated (saw toothed).

*Serration.*—Single, small.

*Rachis.*—Color—Cress Green, Plate 31. Under side—smooth.

*Stipules.*—Medium length, bearded.

*Disease resistance.*—Susceptible to black spot.

Wood:

*New wood.*—Color—Cress Green, Plate 31. Bark—smooth.

*Old wood.*—Color—Dark Cress Green, Plate 31. Bark—smooth.

Thorns (divided into thorns, prickles and short needles):

*Thorns.*—Quantity: on main stalks from base—ordinary; on laterals from stalk—ordinary. Form—broad base, long, hooked downward. Color when young—Liver Brown, Plate 14. Position—three or more.

*Prickles.*—Quantity: on main stalks—few; on laterals—few. Color—Liver Brown, Plate 14.

*Short needles.*—Quantity: on main stalks—none; on laterals—none.

I claim:

A new and distinct variety of rose plant characterized as to novelty by the rich contrasting color combination of its flower, the large size and constancy of the bloom, its sweet persistent fragrance, and its lustrous dark green foliage, substantially as shown and described.

DOMENICO AICARDI.